(12) United States Patent
Affaitati et al.

(10) Patent No.: US 6,432,356 B1
(45) Date of Patent: Aug. 13, 2002

(54) ADAMANTANE DERIVATIVE AND AQUEOUS DISINFECTANT

(75) Inventors: Pietro Affaitati, Albano Laziale; Giancarlo Folchitto, Rome, both of (IT)

(73) Assignee: IMS S.R.L., Pomezia (IT)

( * ) Notice: Subject to any disclaimer, the term of this patent is extended or adjusted under 35 U.S.C. 154(b) by 0 days.

(21) Appl. No.: 09/536,413

(22) Filed: Mar. 28, 2000

(30) Foreign Application Priority Data

Jun. 11, 1999 (IT) ........................................ RM99A0386

(51) Int. Cl.$^7$ ........................ A61L 2/18; A01N 33/26; C07C 245/06
(52) U.S. Cl. .................. 422/28; 534/563; 514/387; 514/393; 424/405; 424/616
(58) Field of Search ................ 422/28; 534/563; 514/387, 393; 424/405, 616

(56) References Cited

U.S. PATENT DOCUMENTS 5,616,335 A * 4/1997 Nicolle et al. .............. 424/405

FOREIGN PATENT DOCUMENTS

EP    0 774 444    5/1997
NL    6700776 A  *  1/1966

OTHER PUBLICATIONS

Derwent Publications Ltd., London, Abstract, XP002147871, SU1246568, Aug. 27, 1995.
Database Xfire [Online], XP002147870, Journal of the Chemical Society, Chemical Communications, No. 10, pp. 625–626, (1985), Letchworth, GB.
Database WPI, "XP002147871", Derwent Publications Ltd. London, GB; section Ch, Week 199616, Class B02, AN 1996–158837.
Database Xfire, "XP002147870", Beilstein Informationssysteme, Frankfurt, DE, registry No. 308161.

* cited by examiner

Primary Examiner—Elizabeth McKane
(74) Attorney, Agent, or Firm—Browdy and Neimark, P.L.L.C.

(57) ABSTRACT

The subject matter of the present invention is the adamantane 5,7-diphenyl-1,3-diazoadamantan-6-one derivative per se and the aqueous disinfectant compositions, characterized in that they contain this molecule, and/or the molecule of at least another adamantane derivative, associated in particular with peracetic acid. The disinfectant compositions according to the invention can be utilized as such or water-diluted at the time of use. The disinfectant compositions according to the invention are sporicidal, bactericidal, fungicidal and virucidal for very short contact times.

8 Claims, No Drawings

ADAMANTANE DERIVATIVE AND AQUEOUS DISINFECTANT

DESCRIPTION

The present invention relates to an adamantane derivative, the 5,7-diphenyl-1,3-diazoadamantan-6-one, per se and to the aqueous disinfectant compositions containing this molecule, and/or the molecule of at least one other adamantane derivative, associated in particular with peracetic acid.

Disinfectant compositions containing, among other components, molecules with adamantane residues, are known in the art.

However, none of the disinfectant compositions as proposed so far contains the 5,7-diphenyl-1,3-diazoadamantan-6-one molecule, and or a molecule of one other adamantane derivative, in particular associated with peracetic acid.

Therefore, a subject of the present invention is the 5,6-diphenyl-1,3-diazoadamantan-6-one molecule, having the following formula (each atom of the adamantane molecule skeleton is conventionally assigned a number; the numbers of the atoms involved in relevant substitutions are given in the formula):

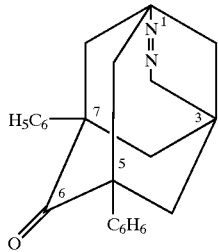

A further subject of the present invention is the use of the 5,7-diphenyl-1,3-diazoadamantan-6-one molecule, and/or the molecule of at least another adamantane derivative, for the formulation of disinfectant compositions. Finally, the aqueous solutions of disinfectant compositions containing the 5,7-diphenyl-1,3-diazoadamantan-6-one molecule, and/or the molecule of another adamantane derivative, associated with peracetic acid, constitute a further subject of the present invention.

The disinfectant composition according to the invention comprises, in one embodiment thereof, the following components, expressed as percent w/v:

| | |
|---|---|
| 5,7-diphenyl-1,3-diazoadamantan-6-one | 0.005–5 |
| peracetic acid | 0.015–15 |
| optionally, phenolic derivatives | ≦10 |
| optionally, additives | ≦50 |
| water as volumetrically needed to | 100. |

The phenolic derivatives can be selected from the group comprising o-phenyl-phenol, p-chloro-m-cresol, 2benzyl-4-chlorophenol, phenol and combinations thereof.

The additives can be selected from the group comprising solvents, sequestering agents, anticorrosives, buffers, perfumes and combinations thereof.

The formulations according to the present invention can be utilised as such or water-diluted at the time of use. Dilutions depend on the required rate of the biocidal action.

The formulations according to the invention proved sporicidal, bactericidal (Gram+ and Gram− Mycobacterium tuberculosis included), fungicidal and virucidal, for very short contact times (starting from 5 minutes). All the microbiological values were tested and are testable according to the CEN TC/216 methods. So far, only a general description of the present invention has been given. With the aid of the examples a more detailed description of some embodiments will be provided hereinafter, finalized to give a better understanding of objects, features, advantages and applications thereof.

EXAMPLE 1

5,7-diphenyl-3-diazoadamantan-6-one-preparation 1.5 moles dibenzylketone, 7.5 moles paraformaldehyde and 3.0 moles ammonium acetate are measured in a round-bottomed flask.

The mixture is dispersed in a volume of ethanol (at least 95°), assessed in the approximate ratio 1:1 with respect to the sum of the reagent weights.

The reaction vessel closed with a fluxing system is brought to boiling onto a water bath. The reagent solubilisation takes place with the temperature increase. Thereafter, the solution becomes red and a crystalline precipitate begins to form. After a 4-hour boiling the reaction is considered to be completed.

The mixture is cooled in a freezer and filtered under vacuum. The raw product is rinsed twice in 950° ethanol, dissolved into a minimum quantity of hot chloroform and filtered.

The filtered solution is diluted with an equal volume of 95° ethanol and left overnight in a freezer. The resulting white crystalline compound is collected on a Buckner, rinsed with 95° ethanol and dried. The evidence of the attainment of the compound according to the invention is provided by the empirical formula $C_{22}H_{20}ON_2$, with a molecular weight of 328 and a melting point of 263–264° C.

Yield: about 25% of the reagent total.

EXAMPLE 2

A disinfectant and sporicidal solution according to the invention has the following composition in percent w/v:

| | |
|---|---|
| 5,7-diphenyl-1,3-diazoadamantan-6-one | 0.050 |
| peracetic acid | 0.100 |
| p-chloro-m-cresol | 0.075 |
| o-phenyl-phenol | 0.005 |
| phenol | 0.100 |
| additives | 15 |
| water as volumetrically needed to | 100 |

EXAMPLE 3

A disinfectant and sporicidal solution according to the invention has the following composition in percent w/v:

| | |
|---|---|
| 5,7-diphenyl-1,3-diazoadamantan-6-one | 0.050 |
| peracetic acid | 0.100 |
| p-chloro-m-cresol | 0.188 |
| additives | 15 |
| water as volumetrically needed to | 100 |

EXAMPLE 4

A disinfectant and sporicidal solution according to the invention has the following composition in percent w/v:

| | |
|---|---|
| 5,7-diphenyl-1,3-diazoadamantan-6-one | 0.050 |
| peracetic acid | 0.150 |
| additives | 15 |
| water as volumetrically needed to | 100 |

EXAMPLE 5

The compositions of the examples 2, 3 and 4 were tested to determine the sporicidal, bactericidal, fungicidal and virucidal activities thereof for different contact times according to the methods set by the CEN TC/216 (Comité Européen de Normalisation, Technical Committee) norms.

Test results confirmed the expected activities.

What is claimed is:

1. The chemical compound 5,7-diphenyl-1,3-diazoadamantan-6-one, having the formula:

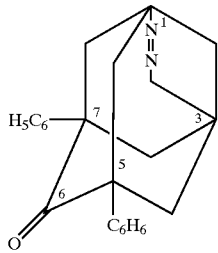

2. In a method of disinfecting comprising applying a disinfectant to a surface to be disinfected, the improvement wherein said disinfectant is 5,7-diphenyl-1,3-diazoadamantan-6-one, according to claim 1.

3. A method according to claim 2, wherein said disinfectant further comprises peracetic acid.

4. A method according to claim 3, wherein said disinfectant further comprises water.

5. Aqueous disinfectant composition, comprising 5,7-diphenyl-1,3-diazoadamantan-6-one according to claim 1, and at least one other adamantane derivative, together with peracetic acid.

6. Aqueous disinfectant composition according to claim 5, having the following composition expressed in percent w/v:

| | |
|---|---|
| 5,7-diphenyl-1,3-diazoadamantan-6-one | 0.005–5 |
| peracetic acid | 0.015–15 |
| optionally, phenolic derivatives | $\leq 10$ |
| optionally, additives | $\leq 50$ |
| water as volumetrically needed to | 100. |

7. Disinfectant composition according to claim 6, wherein at least one phenolic derivative is present and is selected from the group consisting of o-phenyl-phenol, p-chloro-m-cresol, 2-benzyl-4-chlorophenol, phenol and combinations thereof.

8. Disinfectant composition according to claim 7, wherein at least one additive is present and is selected from the group consisting of solvents, requestering agents, anticorrosive agents, buffers, perfumes and combinations thereof.

* * * * *